US011116813B2

(12) United States Patent
Peng et al.

(10) Patent No.: US 11,116,813 B2
(45) Date of Patent: Sep. 14, 2021

(54) ANTIMICROBIAL GARLIC COMPOSITIONS

(71) Applicant: MOOTRAL SA, Rolle (CH)

(72) Inventors: Li Vern Peng, Kuala Lumpur (MY); King Ting Lim, Kuala Lumpur (MY); Patricia De Costa, Kuala Lumpur (MY)

(73) Assignee: MOOTRAL SA, Rolle (CH)

( * ) Notice: Subject to any disclaimer, the term of this patent is extended or adjusted under 35 U.S.C. 154(b) by 0 days.

(21) Appl. No.: 16/495,332

(22) PCT Filed: Mar. 23, 2018

(86) PCT No.: PCT/MY2018/000014
§ 371 (c)(1),
(2) Date: Sep. 18, 2019

(87) PCT Pub. No.: WO2018/182399
PCT Pub. Date: Oct. 4, 2018

(65) Prior Publication Data
US 2020/0016227 A1 Jan. 16, 2020

(30) Foreign Application Priority Data
Mar. 30, 2017 (MY) .............................. PI2017701113

(51) Int. Cl.
| | |
|---|---|
| *A61K 36/8962* | (2006.01) |
| *A23K 20/142* | (2016.01) |
| *A61K 31/10* | (2006.01) |
| *A61K 31/198* | (2006.01) |
| *A61K 33/04* | (2006.01) |

(52) U.S. Cl.
CPC ........ *A61K 36/8962* (2013.01); *A23K 20/142* (2016.05); *A61K 31/10* (2013.01); *A61K 31/198* (2013.01); *A61K 33/04* (2013.01)

(58) Field of Classification Search
None
See application file for complete search history.

(56) References Cited

U.S. PATENT DOCUMENTS

| | | | | |
|---|---|---|---|---|
| 2017/0340691 A1* | 11/2017 | Graz | ................ | A61K 36/8962 |
| 2018/0360773 A1 | 12/2018 | Bjarnsholt et al. | | |
| 2019/0015470 A1* | 1/2019 | Peng | ........................ | A61P 3/02 |

FOREIGN PATENT DOCUMENTS

| | | | |
|---|---|---|---|
| CN | 102423054 | * | 4/2012 |
| WO | WO 2017/119808 A1 | | 7/2017 |

OTHER PUBLICATIONS

Nagourney R. Garlic: Medicinal Food or Nutritious Medicine? J of Medicinal Food 1(1)13-28, 1998. (Year: 1998).*
Maldonado, P. et al. Medicinal Properties of Garlic Garlic Consumption and Health by Nova Science Publishers 61-116, 2010. (Year: 2010).*
Weber, N. et al. In vitro Virucidal Effects of Allium Sativum Extract and Compounds Planta Medica 58(5)417-423, 1992. (Year: 1992).*
U.S. Patent Office, English language version of the International Search Report, Form PCT/ISA/210 for International Application PCT/MY2018/000014, dated Sep. 5, 2018 (5 pages).
U.S. Patent Office, English language version of the Written Opinion of the International Searching Authority, Form PCT/ISA/237 for International Application PCT/MY2018/000014, dated Sep. 5, 2018 (8 pages).
https://www.wikihow.com/Make-Garlic-Paste,"wikiHow, How to Make Garlic Paste", Aug. 27, 2018, (4 pages).
https://www.wikihow.com/Caramelize-Garlic,"wikiHow, How to Caramelize Garlic", Aug. 27, 2018, (6 pages).
Hughes et al.,"Antimicrobial Effects of *Album sativum* L. (Garlic), *Allium ampeloprasum* L. (Elephant Garlic), and *Allium cepa* L. (Onion), Garlic Compounds and Commercial Garlic Supplement Products," Phytotherapy Research, vol. 5, No. 4, Aug. 1, 1991, pp. 154-158.
Rahman et al.,"Assessment of the Anti-Microbial Activity of Dried Garlic Powders Produced by Different Methods of Drying," International Journal of Food Properties, vol. 9, No. 3, Sep. 1, 2006, pp. 503-513.
Kimura et al.,"Black garlic: A critical review of its production, bioactivity, and application," Journal of Food and Drug Analysis, vol. 25, No. 1, Dec. 5, 2016, pp. 62-70.
In-Chang Jung et al.,"Antioxidation, Antimicrobial and Antithrombosis Activities of Aged Black Garlic (*Allium sativum* L.)," Korean Journal of Microbiology and Biotechnology, vol. 42, No. 3, Sep. 28, 2014, pp. 285-292.
Fratianni et al.,"Biochemical Characterization and Antimicrobial and Antifungal Activity of Two Endemic Varieties of Garlic (*Allium sativum* L.) of the Campania Region, southern Italy," Journal of Medicinal Food, Apr. 11, 2016. pp. 1-6.

* cited by examiner

*Primary Examiner* — Ralph J Gitomer
(74) *Attorney, Agent, or Firm* — Pauley Erickson & Swanson

(57) ABSTRACT

A composition of a first garlic extract and a second garlic extract that is different to the first garlic extract. The composition is useful as an antimicrobial, such as in pharmaceutical compositions including the first garlic extract and the second garlic extract. The invention further includes methods for making said compositions and pharmaceutical compositions.

20 Claims, No Drawings

ANTIMICROBIAL GARLIC COMPOSITIONS

TECHNICAL FIELD

The present invention is directed to a composition comprising at least two different garlic extracts, and to the use of said composition as an antimicrobial (e.g. to inhibit growth of or reduce growth of or to kill microbes). The compositions may be used for both therapeutic and non-therapeutic methods, for example to treat or prevent a microbial infection in a subject.

BACKGROUND OF THE INVENTION

Antimicrobial compositions are widely used to kill and/or inhibit or reduce the growth of microbes such as bacteria, fungi and viruses. For example, antimicrobial compositions may be used against microbes on non-living surfaces, for example to prevent the spread of illness, or may be used against microbes on living surfaces or may be administered to a subject to treat or prevent microbial infection in a subject. It is therefore desirable to provide new antimicrobial compositions for these uses. It is particularly desirable to provide new antimicrobial compositions since microbes are increasingly developing resistance to known antimicrobial compositions.

SUMMARY OF THE INVENTION

The present invention is based, at least on part, on the surprising finding that compositions comprising at least two different garlic extracts act as an antimicrobial.

According to a first aspect, there is provided a use of composition comprising a first garlic extract and a second garlic extract different to the first garlic extract as an antimicrobial. The use may, for example, be therapeutic or non-therapeutic.

According to a second aspect, there is provided an antimicrobial composition comprising a first garlic extract and a second garlic extract different to the first garlic extract. In certain embodiments, the composition consists essentially of or consists of a first garlic extract and a second garlic extract different to the first garlic extract. In certain embodiments, the composition is a nutraceutical composition.

According to a third aspect, there is provided a pharmaceutical composition comprising an antimicrobial composition according to any aspect or embodiment of the invention (e.g. a composition comprising, consisting essentially of or consisting of a first garlic extract and a second garlic extract) and a pharmaceutically acceptable excipient and/or carrier and/or diluent.

According to a fourth aspect, there is provided a use of a composition or pharmaceutical composition according to any aspect or embodiment of the invention as an antimicrobial. In certain embodiments, the use is therapeutic. In certain embodiments, the use is non-therapeutic. In certain embodiments, the use is to treat or prevent a microbial infection in a subject.

According to a fifth aspect, there is provided a composition or pharmaceutical composition according to any aspect or embodiment of the invention for use as an antimicrobial. In certain embodiments, the use is therapeutic. In certain embodiments, the use is non-therapeutic. In certain embodiments, the use is to treat or prevent a microbial infection in a subject.

According to a sixth aspect, there is provided a use of a composition or pharmaceutical composition according to any aspect or embodiment of the invention in the manufacture of a medicament for treating or preventing a microbial infection in a subject.

According to a seventh aspect, there is provided a method for inhibiting or reducing the growth of one or more microbes and/or for reducing the number of microbes. In certain embodiments, the method is therapeutic. In certain embodiments, the method is to treat or prevent a microbial infection in a subject. In certain embodiments, the method is non-therapeutic.

Embodiments of the invention will be further described in the detailed description. Any embodiment described herein or any combination of embodiments described herein is applicable to any one or more aspects of the present invention unless stated otherwise or clearly contradicted by context.

DETAILED DESCRIPTION OF THE INVENTION

The present invention is based, at least on part, on the surprising finding that compositions comprising at least two different garlic extracts act as an antimicrobial.

Hereinafter, the invention shall be described according to preferred embodiments of the present invention and by referring to the accompanying description. However, it is to be understood that limiting the description to the preferred embodiments of the invention is merely to facilitate discussion of the present invention and it is envisioned that those skilled in the art may devise various modifications without departing from the scope of the appended claims.

The terms generally used hereinbefore and hereinafter have for preference the meanings indicated below, unless indicated otherwise, whereby more specific meanings may be used independently of one another in preferred embodiments of the present inventions instead of the general definitions, these more specific significances describing especially preferred embodiments of the invention.

Where the term "at least one" or "one or more" occurs hereinbefore and hereinafter. this signifies in particular one to ten, for preference one to three, and in particular one or, further, two of the features enumerated, such as components. Where ranges are indicated, such as weight percentage ranges, these include the limit values indicated; thus, for example, "between X and Y" signifies "from and including X up to and including Y".

The term "product" or "composition" may mean in particular a pharmaceutical product or pharmaceutical composition in the sense of a formulation, whereby this term is not restricted to pharmaceutical products suitable for registration, or a medical product or fictitious pharmaceuticals. The "product" or "composition" may refer to a nutraceutical product. The "product" or "composition" may refer to a cosmetic product. The product or composition may, for example, be a solid, semi-solid (e.g. gel, ointment, cream, paste) or liquid product or composition.

The term "therapeutic treatment" or "therapeutic method", also includes prophylaxis and the alleviation of symptoms of a disease and/or disorder in a subject, although not cosmetic treatments.

The term "nutraceutical" refers to a food or part of a food that includes, but is not limited to, dietary supplements, functional foods and medicinal foods. It is known in the field of art that a "nutraceutical" can be used in a therapeutic treatment and/or non-therapeutic treatment depending on the desires and/or needs of a subject.

The expression "treating or preventing" and analogous terms used herein refers to all forms of healthcare intended to remove or avoid the disease and/or disorder or to relieve its symptoms, including preventive and curative care, as judged according to any of the tests available according to the prevailing medical practice. An intervention that aims with reasonable expectation to achieve a particular result but does not always do so is included within the expression "treating or preventing". An intervention that succeeds in slowing or halting progression of a disease and/or disorder is included within the expression "treating or preventing".

The components referred to hereinbefore and hereinafter are in particular selected from among those such as are listed in pharmacopoeia, e.g. in the US Pharmacopoeia National Formulary, the Pharmacopoea Europea, the Pharmacopoea Helvetica, the British Pharmacopoeia, the German Pharmacopoeia, the Chinese Pharmacopoeia, the Japanese Pharmacopoeia, or supplements, such as by way of decrees.

The term "consisting of" may, for example, exclude any additional element, step or ingredient not explicitly recited.

The term "consisting essentially of" may, for example, exclude any additional element, step or ingredient not explicitly recited unless the additional element, step or ingredient does not materially affect the basic and novel properties of the invention. Where the one or more additional element(s), step(s) or ingredient(s) is/are one or more additional component(s) of a composition or pharmaceutical composition, the total amount of the additional component(s) in the composition may, for example, be limited to 20 wt %. For example, the total amount of the additional component(s) in the composition may be limited to 19 wt % or 18 wt % or 17 wt % or 16 wt % or 15 wt % or 14 wt % or 13 wt % or 12 wt % or 11 wt % or 10 wt % or 9 wt % or 8 wt % or 7 wt % or 6 wt % or 5 wt % or 4 wt % or 3 wt % or 2 wt % or 1 wt %.

The composition or pharmaceutical composition comprises a first garlic extract and a second garlic extract different from the first garlic extract. The composition or pharmaceutical composition may also further comprise one or more further garlic extracts, which may be different to the first and second garlic extracts. For example, the composition or pharmaceutical composition may further comprise a third garlic extract or further comprise a third and fourth garlic extract or further comprise a third, fourth and fifth garlic extract or further comprise a third, fourth, fifth and sixth garlic extract. In certain embodiments, the composition consists essentially of or consists of the garlic extracts. For example, the composition may consist essentially of or consist of the first garlic extract and the second garlic extract. For example, the composition may consist essentially of or consist of the first garlic extract, the second garlic extract and the third garlic extract.

The term "garlic extract" encompasses aqueous garlic extract, non-aqueous garlic extract (solvent garlic extract), alcoholic garlic extract, garlic concentrate, garlic oil, garlic maceration, garlic powder, garlic granules and any combination of two or more thereof. Hereinafter, the invention may tend to be described in terms of aqueous garlic extracts. However, the invention should not be construed as being limited to such embodiments. Each garlic extract may, for example, be derived from fresh or non-aged garlic. Alternatively, each garlic extract may, for example, be derived from aged garlic.

Each garlic extract may independently be derived from any of the subspecies and varieties of *Allium* spp., particularly garlic (*Allium sativum*) that are currently known or are later discovered. Besides, garlic extracts intended to be used in the present composition can also be obtained from other *Allium* spp., such as *Allium ursinum, Allium fistulosum*, and *Allium tricoccum*. For example, each garlic extract may independently be derived from garlic of the subspecies ophioscorodon (hard neck garlic) and sativum (soft neck garlic). For example, each garlic extract may independently be derived from porcelain garlics, rocambole garlics, purple stripe garlics, marbled purple stripe garlics, glazed purple stripe garlics, artichoke garlics, silverskin garlics, asiatic garlics, turban garlics and creole garlics.

Each garlic extract may independently be derived from any form of garlic. For example, each garlic extract may independently be derived from raw garlic, aqueous garlic extract, non-aqueous garlic extract, alcoholic garlic extract, garlic concentrate, garlic oil, garlic maceration, garlic powder or garlic granules. According to one of the embodiments of the present invention, each garlic extract may independently be derived from a garlic that has been treated or processed before the extract is obtained, i.e. aged garlic; or a garlic that has not been treated or processed before the extract is obtained, i.e. fresh or non-aged garlic.

For example, each garlic extract may independently be derived from "aged garlic" or "black garlic". In general, aged garlic (including black garlic) can be obtained when the garlic bulbs have been stored in a controlled condition and heated under specific temperature, humidity and solvents, for example over several days or weeks, to cause the cloves to darken in colour after undergoing Millard or browning reaction. For example, the type of garlic extract generally known by the term "aged garlic" is obtained by storing the garlic bulbs with alcohol for a few weeks (e.g. 2 weeks) up to about 2 years (e.g. 20 months). Contrarily, the manufacturing process of black garlic does not involve the alcoholic ageing step. Black garlic is obtained by storing the garlic bulbs with water for approximately 1 month under relatively high temperature (e.g. greater than 50° C.).

Fresh or non-aged garlic extract refers to extract derived from garlic bulbs without undergoing special treatment or process intentionally to transform or convert its constituents into different compounds. In certain embodiments, each garlic extract may independently be derived from fresh or non-aged garlic that may have been treated or processed by a method other than that used to make "aged garlic" or "black garlic". For example, the fresh or non-aged garlic extract can be processed or treated to reduce or remove the garlic odour. Such garlic extract is generally known as deodourised garlic extract. Generally, an encapsulation or coating process can be applied to mask or reduce the garlic odour. Alternatively, taste-masking ingredients such as green tea, parsley, basil, spinach etc. can be added to mask or reduce the garlic odour in a composition.

Hereinafter, the invention may tend to be discussed in terms of at least one aged garlic extract and at least one non-aged garlic extract. In certain embodiments, the aged garlic extract can be a black garlic extract, caramelised garlic extract and/or fermented garlic extract, for example black garlic powder extract (BGPE). In certain embodiments, the non-aged garlic extract can be deodourised garlic extract, for example deodorised garlic powder extract (DGPE).

Alternatively or additionally, the invention may tend to be discussed in terms of at least one black garlic extract and at least one deodorized garlic extract. For example, the invention may tend to be discussed in terms of at least one black garlic powder extract (BGPE) and at least one deodorized garlic powder extract (DGPE). However, the invention should not be construed as being limited to such embodiments.

The weight ratio of the first garlic extract to the second garlic extract may range from about 1:2000 to about 100:1. For example, the weight ratio of the first garlic extract to the second garlic extract may range from about 1:1900 to about 95:1, for example from about 1:1800 to about 90:1, for example from about 1:1700 to about 85:1, for example from about 1:1600 to about 80:1, for example from about 1:1500 to about 75:1, for example from about 1:1400 to about 70:1, for example from about 1:1300 to about 65:1, for example from about 1:1200 to about 60:1, for example from about 1:1100 to about 60:1, for example from about 1:1000 to about 60:1, for example from about 16:1 to about 1:16.

For example, the first garlic extract may be an aged garlic extract and the second garlic extract may be a non-aged garlic extract and the weight ratio of the first garlic extract to the second garlic extract may range from about 1:2000 to about 100:1, for example from about 1:1900 to about 95:1, for example from about 1:1800 to about 90:1, for example from about 1:1700 to about 85:1, for example from about 1:1600 to about 80:1, for example from about 1:1500 to about 75:1, for example from about 1:1400 to about 70:1, for example from about 1:1300 to about 65:1, for example from about 1:1200 to about 60:1, for example from about 1:1100 to about 60:1, for example from about 1:1000 to about 60:1, for example from about 16:1 to about 1:16.

For example, the first garlic extract may be BGPE and the second garlic extract may be DGPE and the weight ratio of the first garlic extract to the second garlic extract may range from about 1:2000 to about 100:1, for example from about 1:1900 to about 95:1, for example from about 1:1800 to about 90:1, for example from about 1:1700 to about 85:1, for example from about 1:1600 to about 80:1, for example from about 1:1500 to about 75:1, for example from about 1:1400 to about 70:1, for example from about 1:1300 to about 65:1, for example from about 1:1200 to about 60:1, for example from about 1:1100 to about 60:1, for example from about 1:1000 to about 60:1, for example from about 16:1 to about 1:16.

Each garlic extract may comprise one or more of allicin, polyphenol, alliin, γ-glutamylcysteine, S-allyl-L-cysteine, other thiosulfinates and sulfur compounds. For example, each garlic extract may comprise all of allicin, polyphenol, alliin, γ-glutamylcysteine and S-allyl-L-cysteine. For example, each garlic extract may comprise all of allicin, polyphenol, alliin, γ-glutamylcysteine, S-allyl-L-cysteine, other thiosulfinates and sulfur compounds. In certain embodiments, the first garlic extract, for example aged garlic extract such as BGPE, contains mainly polyphenol; whereas the second garlic extract, for example non-aged garlic extract such as DGPE, contains mainly allicin. The amount of allicin is standardised based on allicin yield or allicin potential as it is known in the art that allicin is not present in an intact garlic bulb, garlic powder or aqueous garlic powder. It is only present when fresh garlic is crushed or when the garlic powder extract is dissolved in water. In certain embodiments, at least one of the first and second garlic extracts comprises at least about 3 wt % allicin. In certain embodiments, the first garlic extract is a non-aged (white) garlic extract such as DGPE and comprises at least about 3 wt % allicin. In certain embodiments, at least one of the first and second garlic extracts comprises at least about 5 wt % polyphenol. In certain embodiments, the second garlic extract is an aged garlic extract such as BGPE and comprises at least about 5 wt % polyphenol.

The composition or pharmaceutical composition may comprise one or more of allicin, polyphenol, alliin, γ-glutamylcysteine, S-allyl-L-cysteine, other thiosulfinates, sulfur compounds. For example, the composition or pharmaceutical composition may comprise all of allicin, polyphenol, alliin, γ-glutamylcysteine and S-allyl-L-cysteine. For example, the composition or pharmaceutical composition may comprise all of allicin, polyphenol, alliin, γ-glutamylcysteine, S-allyl-L-cysteine, other thiosulfinates and sulfur compounds.

The composition (e.g. the combination of the garlic extracts, such as the first and second garlic extracts) may comprise equal to or greater than about 0.5% (w/w) allicin. For example the composition (e.g. the combination of the garlic extracts (e.g. the first and second garlic extract components)) may together comprise equal to or greater than about 1.0% (w/w) allicin. For example, the composition (e.g. the combination of the garlic extracts (e.g. the first and second garlic extracts)) may comprise equal to or greater than about 1.5% (w/w), for example equal to or greater than about 2.0% (w/w), for example equal to or greater than about 2.5% (w/w), for example equal to or greater than about 3.0% (w/w), for example equal to or greater than about 3.5% (w/w), for example equal to or greater than about 3.5% (w/w), for example equal to or greater than about 4.0% (w/w), for example equal to or greater than about 4.5% (w/w), for example equal to or greater than about 5.0% (w/w) allicin. For example, the composition (e.g. the combination of the garlic extracts (e.g. the first and second garlic extracts)) may comprise up to about 10.0% (w/w) allicin, for example up to about 8.0% (w/w) allicin, for example up to about 6.0% (w/w) allicin.

The composition (e.g. the combination of the garlic extracts such as the first and second garlic extracts) may comprise equal to or greater than about 0.5% (w/w) polyphenol. For example, the composition (e.g. the combination of the garlic extracts (e.g. the first and second garlic extract components)) may together comprise equal to or greater than about 1.0% (w/w) polyphenol. For example, the composition (e.g. the combination of the garlic extracts (e.g. the first and second garlic extracts)) may comprise equal to or greater than about 1.5% (w/w), for example equal to or greater than about 2.0% (w/w), for example equal to or greater than about 2.5% (w/w), for example equal to or greater than about 3.0% (w/w), for example equal to or greater than about 3.5% (w/w), for example equal to or greater than about 3.5% (w/w), for example equal to or greater than about 4.0% (w/w), for example equal to or greater than about 4.5% (w/w), for example equal to or greater than about 5.0% (w/w) polyphenol. For example, the composition (e.g. the combination of the garlic extracts (e.g. the first and second garlic extracts)) may comprise up to about 10.0% (w/w) polyphenol, for example up to about 8.0% (w/w) polyphenol, for example up to about 6.0% (w/w) polyphenol.

The composition, (e.g. the combination of the garlic extracts such as the first and second garlic extracts) may comprise equal to or greater than about 0.5% (w/w) total thiosulfinates. For example, the composition (e.g. the combination of the garlic extracts (e.g. the first and second garlic extract components)) may together comprise equal to or greater than about 1.0% (w/w) total thiosulfinates. For example, the composition (e.g. the combination of the garlic extracts (e.g. the first and second garlic extracts)) may comprise equal to or greater than about 1.5% (w/w), for example equal to or greater than about 2.0% (w/w), for example equal to or greater than about 2.5% (w/w), for example equal to or greater than about 3.0% (w/w), for example equal to or greater than about 3.5% (w/w), for example equal to or greater than about 3.5% (w/w), for example equal to or greater than about 4.0% (w/w), for example equal to or greater than about 4.5% (w/w), for example equal to or greater than about 5.0% (w/w) total thiosulfinates. For example, the composition (e.g. the combination of the garlic extracts (e.g. the first and second garlic extracts)) may comprise up to about 10.0% (w/w) total thiosulfinates, for example up to about 8.0% (w/w) total thiosulfinates, for example up to about 6.0% (w/w) total thiosulfinates.

The composition, (e.g. the combination of the garlic extracts such as the first and second garlic extracts) may comprise equal to or greater than about 1.5% (w/w) alliin. For example, the composition (e.g. the combination of garlic extracts (e.g. the first and second garlic extract components)) may together comprise equal to or greater than about 2.0% (w/w) alliin. For example, the composition (e.g. the combination of the garlic extracts (e.g. the first and second garlic extracts) may comprise equal to or greater than about 2.5% (w/w), for example equal to or greater than about 2.7% (w/w), for example equal to or greater than about 3.2% (w/w), for example equal to or greater than about 3.5% (w/w), for example equal to or greater than about 4.0% (w/w), for example equal to or greater than about 4.5% (w/w), for example equal to or greater than about 5.0% (w/w), for example equal to or greater than about 5.5% (w/w), for example equal to or greater than about 6.0% (w/w), for example equal to or greater than about 6.5% (w/w), for example equal to or greater than about 7.0% (w/w) alliin. For example, the composition (e.g. the combination of garlic extracts (e.g. the first and second garlic extracts)) may comprise up to about 12.0% (w/w) alliin, for example up to about 10.0% (w/w) alliin, for example up to about 8.0% (w/w) alliin.

The composition, (e.g. the combination of the garlic extracts such as the first and second garlic extracts) may comprise equal to or greater than about 1.5% (w/w) γ-glutamylcysteine. For example, the composition (e.g. the combination of the garlic extracts (e.g. the first and second garlic extract components)) may together comprise equal to or greater than about 2.0% (w/w) γ-glutamylcysteine. For example, the composition (e.g. the combination of the garlic extracts (e.g. the first and second garlic extracts)) may comprise equal to or greater than about 2.5% (w/w), for example equal to or greater than about 3.0% (w/w), for example equal to or greater than about 4.0% (w/w), for example equal to or greater than about 4.5% (w/w), for example equal to or greater than about 5.0% (w/w), for example equal to or greater than about 5.5% (w/w), for example equal to or greater than about 6.0% (w/w), for example equal to or greater than about 6.5% (w/w), for example equal to or greater than about 7.0% (w/w), for example equal to or greater than about 7.5% (w/w) γ-glutamylcysteine. For example, the composition (e.g. the combination of the garlic extracts (e.g. the first and second garlic extracts)) may comprise up to about 12.0% (w/w) γ-glutamylcysteine, for example up to about 10.0% (w/w) γ-glutamylcysteine, for example up to about 8.0% (w/w) γ-glutamylcysteine.

The composition (e.g. the combination of the garlic extracts such as the first and second garlic extracts) may comprise equal to or greater than about 0.3% (w/w) total sulfur. For example, the composition (e.g. the combination of the garlic extracts (e.g. the first and second garlic extract components)) may together comprise equal to or greater than about 0.6% (w/w) total sulfur. For example, the composition (e.g. the combination of the garlic extracts (e.g. the first and second garlic extracts)) may comprise equal to or greater than about 1.0% (w/w), for example equal to or greater than about 1.5% (w/w), for example equal to or greater than about 2.0% (w/w), for example equal to or greater than about 2.5% (w/w), for example equal to or greater than about 3.0% (w/w), for example equal to or greater than about 3.5% (w/w), for example equal to or greater than about 4.0% (w/w), for example equal to or greater than about 4.5% (w/w) total sulfur. For example, the composition (e.g. the combination of the garlic extracts (e.g. the first and second garlic extracts)) may comprise up to about 10.0% (w/w) total sulfur, for example up to about 8.0% (w/w) total sulfur, for example up to about 6.0% (w/w) total sulfur.

The composition (e.g. the combination of the garlic extracts such as the first and second garlic extracts) may comprise equal to or greater than about 0.05% (w/w) S-allyl-L-cysteine. For example, the composition (e.g. the combination of the garlic extracts (e.g. the first and second garlic extract components)) may together comprise equal to or greater than about 0.1% (w/w) S-allyl-L-cysteine or equal to or greater than about 0.15% (w/w) S-allyl-L-cysteine. For example, the composition (e.g. the combination of the garlic extracts (e.g. the first and second garlic extracts)) may comprise equal to or greater than about 0.2% (w/w), for example equal to or greater than about 0.3% (w/w), for example equal to or greater than about 0.5% (w/w), for example equal to or greater than about 0.7% (w/w), for example equal to or greater than about 1.0% (w/w), for example equal to or greater than about 1.2% (w/w), for example equal to or greater than about 1.5% (w/w), for example equal to or greater than about 1.7% (w/w), for example equal to or greater than about 2.0% (w/w) S-allyl-L-cysteine. For example, the composition (e.g. the combination of the garlic extracts (e.g. the first and second garlic extracts)) may comprise up to about 10.0% (w/w) S-allyl-L-cysteine, for example up to about 8.0% (w/w) S-allyl-L-cysteine, for example up to about 6.0% (w/w) S-allyl-L-cysteine, for example up to about 5.0% (w/w) S-allyl-L-cysteine.

The composition (e.g. the combination of the garlic extracts such as the first and second garlic extracts) may comprise equal to or greater than about 0.5% (w/w) allicin and/or equal to or greater than about 0.5% (w/w) polyphenol and/or equal to or greater than about 0.5% (w/w) total thiosulfinates and/or equal to or greater than about 1.5% (w/w) alliin and/or equal to or greater than about 1.5% (w/w) γ-glutamylcysteine and/or equal to or greater than about 0.3% (w/w) total sulfur and/or equal to or greater than about 0.05% (w/w) S-allyl-L-cysteine. The composition may, for example, comprise all of these components in the stated amounts.

The composition (e.g. the combination of the garlic extracts such as the first and second garlic extracts) may comprise equal to or greater than about 0.5% (w/w) allicin and/or equal to or greater than about 0.5% (w/w) polyphenol and/or equal to or greater than about 0.5% (w/w) total thiosulfinates and/or equal to or greater than about 1.5% (w/w) alliin and/or equal to or greater than about 1.5% (w/w) γ-glutamylcysteine and/or equal to or greater than about 0.3% (w/w) total sulfur and/or equal to or greater than about 0.15% (w/w) S-allyl-L-cysteine. The composition may, for example, comprise all of these components in the stated amounts.

The composition (e.g. the combination of the garlic extracts such as the first and second garlic extracts) may comprise equal to or greater than about 0.7% (w/w) allicin and/or equal to or greater than about 0.7% (w/w) polyphenol and/or equal to or greater than about 0.7% (w/w) total thiosulfinates and/or equal to or greater than about 1.6% (w/w) alliin and/or equal to or greater than about 1.5% (w/w) γ-glutamylcysteine and/or equal to or greater than about 0.3% (w/w) total sulfur and/or equal to or greater than about 0.05% (w/w) S-allyl-L-cysteine. The composition may, for example, comprise all of these components in the stated amounts.

The composition (e.g. the combination of the garlic extracts such as the first and second garlic extracts) may comprise equal to or greater than about 1.5% (w/w) allicin and/or equal to or greater than about 1.5% (w/w) polyphenol and/or equal to or greater than about 1.5% (w/w) total thiosulfinates and/or equal to or greater than about 3.2% (w/w) alliin and/or equal to or greater than about 3.0% (w/w) γ-glutamylcysteine and/or equal to or greater than about 0.6% (w/w) total sulfur and/or equal to or greater than about 0.15% (w/w) S-allyl-L-cysteine. The composition may, for example, comprise all of these components in the stated amounts.

The composition or pharmaceutical composition may further comprise dietary fibre of plant and/or non-plant origin. The term "dietary fibre" used herein has its normal meaning for this term. It is generally regarded as the indigestible portion of food derived from plants. Typically, there are two main components of dietary fibre: soluble fibre, which dissolves in water, and insoluble fibre, which does not dissolve in water. Soluble fibres include inulin, chitosan, gum acacia, guar gum, low-methoxy and high-methoxy pectin, oat and/or barley beta glucans, carrageenan, psyllium, cyclodextrin, and derivatives thereof. Insoluble fibres include oat hull fibre, pea hull fibre, soy hull fibre, soy cotyledon fibre, sugar beet fibre, cellulose, corn bran and derivatives thereof. The composition may comprise from about 0.1% to about 90% by weight of dietary fibre, for example, from about 1% to about 80% by weight, or from about 1% to about 70% by weight, or from about 1% to about 60% by weight, or from about 1% to about 50% by weight, or from about 5% to about 50% by weight, or from about 10% to about 50% by weight, or from about 20% to about 50% by weight by weight of dietary fibre, based on the total weight of the composition or pharmaceutical composition.

The composition or pharmaceutical composition may further comprise naturally-derived active ingredients such as plant or fruit extracts, for example leaf extracts (e.g. herbs of *Curcuma* spp. *Andrographis* spp, etc), fruit extracts (e.g. melon extracts, mango extracts, grape extracts, etc), seed extracts (e.g. grape seed extract, guarana extract, etc). In certain embodiments, the composition or pharmaceutical composition may further comprise flavonoids, bioflavonoids (e.g. quercetin, rutinosides) or phytonutrients. Other active ingredients (which may or may not be derived from plant or fruit extracts), which can also be combined with the composition or pharmaceutical composition of the present invention, include chlorella, collagen spirulina, hyaluronic acid, CoQ-10, plant sterol, beta glucan, red yeast rice, resveratrol, astaxanthin, lutein, glutathione, anthocyanidin, cranberry, bilberry, blueberry, lycopene, flaxseed, fatty acids, lecithin, melatonin, glucosamine, chondroitin, ashwagandha, asparagus extract, saffron extract, tart cherry powder, lemon verbena extract, capsicum spp., ginseng, green tea extract, beetroot, ginger extract, phosphatidylcholine, rosemary extract, schisandra extract, guava leaf extract, bentonite, ginkgo biloba, amino acids, caffeine, olive extract, goji extract, pomegranate, astragalus, reishi mushroom, bacopa, colostrum, GABA and echinaceae. The composition may comprise from about 0.1% to about 90% by weight of such additional active ingredients, for example, from about 1% to about 80% by weight, or from about 1% to about 70% by weight, or from about 1% to about 60% by weight, or from about 1% to about 50% by weight, or from about 5% to about 50% by weight, or from about 10% to about 50% by weight, or from about 20% to about 50% by weight, based on the total weight of the composition or pharmaceutical composition.

The composition or pharmaceutical composition may further comprise other biologically active agents, for example, biologically active agents suitable for killing and/or inhibiting or reducing growth of microbes. For example, the composition or pharmaceutical composition may further comprise one or more microbiocidals (agents that kill microbes) and/or one or more biostatics (agents that inhibit growth of microbes). For example, the composition or pharmaceutical composition may further comprise one or more antibiotic agents and/or one or more antifungal agents and/or one or more antiviral agents. For example, the composition or pharmaceutical composition may further comprise one or more naturally-occurring antimicrobial agents. In certain embodiments, the biologically active agent or agents are present in the composition or pharmaceutical composition in an amount ranging from about 0.001 wt. % to about 50 wt. %, based on the total weight of the composition, for example, about 0.1 wt. % to about 15 wt. %, or from about 0.5 wt. % to about 10 wt, %, or from about 0.5 wt. % to about 5 wt. %, or from about 0.1 wt. % to about 3 wt. %, or from about 0.1 wt. % to about 2 wt. %, or from about 0.1 wt. % to about 1 wt. %, or from about 0.001 wt. % to about 5 wt. %, or from about 0.001 wt. % to about 2 wt. %, or from about 0.001 wt. % to about 1 wt. %, or from about 0.001 wt. % to about 0.5 wt. %, or from about 0.001 wt. % to about 0.1 wt. %, or from about 0.001 wt. % to about 0.01 wt. %.

The composition or pharmaceutical composition may further comprise a nutrient ingredient selected from the group consisting of vitamins and minerals, and combinations thereof. The vitamin may be any one or more of vitamin A, vitamin D, vitamin E, vitamin K, thiamine, riboflavin, pyridoxine, cyanocobalamin, carotenoids (including beta-carotene, zeaxanthin, lutein and lycopene), niacin, folic acid, pantothenic acid, biotin, vitamin C, choline, inositol, and salts and derivatives thereof. The mineral may be any one or more of calcium, phosphorous, magnesium, iron, zinc, manganese, copper, cobalt, boron, iodine, sodium, potassium, molybdenum, selenium, chromium, fluorine and chloride. If present, the composition or pharmaceutical composition may comprise from about 0.0001% to about 50% by weight of vitamin(s) and/or mineral(s), based on the total weight of the composition, for example, from about 0.01% to about 45% by weight, from about 0.1% to about 40% by weight, or from about 0.5% to about 30% by weight, or from about 0.5% to about 20% by weight, or from about 0.5% to about 10% by weight, or from about 0.5% to about 5%, or 20 from about 0.5% to about 3%, or from about 0.1% to about 2%, or from about 0.1 to about 1% of vitamin(s) and/or mineral(s), based on the total weight of the composition or pharmaceutical composition. The composition may comprise from about 0.0001% to about 5 wt. %, for example, from about 0.0001% to about 2 wt. %, or from about 0.0001% to about 1 wt. %, or from about 0.0001% to about 0.5 wt. %, or from about 0.0001% to about 0.1 wt. %, or from about 0.0001% to about 0.01 wt. % by weight of vitamin(s) and/or mineral(s), based on the total weight of the composition or pharmaceutical composition.

The composition or pharmaceutical composition of the present invention may be administered in the form of a composition comprising any suitable additional component. The composition may, for example, be a pharmaceutical composition (medicament), suitable for oral, nasal, topical, suppository, intravenous or intradermal administration. The composition may alternatively be a nutraceutical composition, for example, a foodstuff, food supplement, dietary supplement, health supplement, meal replacement product, beverage, beverage supplement, food additive, animal feed or feed additive.

The term "pharmaceutical composition" or "medicament" in the context of this invention means a composition comprising (a pharmaceutically effective amount of) garlic extracts and additionally one or more pharmaceutically acceptable carriers and/or excipients and/or diluents. The pharmaceutical composition may further contain ingredients selected from, for example, diluents, adjuvants, excipients, vehicles, preserving agents, fillers, binders, disintegrating agents, wetting agents, emulsifying agents, suspending agents, sweetening agents, flavouring agents, perfuming agents, antibacterial agents, antifungal agents, lubricating agents, coating agents, encapsulating agents and dispersing agents, depending on the nature of the mode of administration and dosage forms. The pharmaceutical compositions may take the form, for example, of solid preparations including tablets, capsules, caplets, drageés, lozenges, granules, powders, pellets, beads and cachets; and liquid preparations including elixirs, syrups, suspensions, sprays, emulsions, lotions, creams and solutions. Techniques and formulations generally may be found in Remington, The Science and Practice of Pharmacy, Mack Publishing Co., Easton, Pa., latest edition.

In solid dosage forms of the invention for oral administration, the active ingredient(s) may be mixed with one or more pharmaceutically acceptable carriers, such as dicalcium phosphate, and/or any of the following: diluents, fillers or extenders, such as starches, lactose, sucrose, glucose, dextrates, mannitol, microcrystalline cellulose and/or silicic acid; binders, such as, for example, hydroxypropylcellulose, hypromellose, hydroxypropyl methylcellulose, polyglycol such as polyethylene glycol, carboxymethylcellulose, gelatine, polyvinyl pyrrolidones, polyvinyl acetate, sucrose and/or acacia; disintegrating agents, such as starch, for example, potato or tapioca starch, starch derivatives such as sodium starch glycolate, crospolyvinylpyrollidone, calcium carbonate, croscarmellose sodium, alginic acid, silicone dioxide, and certain silicates; lubricants, such as talc, calcium stearate, magnesium stearate, stearic acid, sodium sulfate stearyl fumarate, solid polyethylene glycols, solubiliser such as sodium lauryl sulfate, flavouring and colouring agents and mixtures thereof.

Tablets, and other solid dosage forms of the pharmaceutical compositions of the invention, may optionally be prepared with coatings and shells, such as enteric coatings and other coatings well known in the pharmaceutical-formulation art. They may also be formulated so as to provide slow or controlled release of the active ingredient(s) therein using, for example, natural and synthetic polymers such as hydroxypropylmethyl cellulose methacrylates, methacrylic acid copolymers (e.g. methyl acrylate-methacrylic acid copolymers and methyl methacrylate-methacrylic acid copolymers), shellac, ethylcellulose, cellulose acetate phthalate, cellulose acetate trimellitate, polyvinyl acetate phthalate, cellulose acetate succinate, hydroxyl propyl methyl cellulose acetate succinate, sodium alginate, waxes, fatty acids, zein, respectively, in varying proportions to provide the desired release profile, other polymer matrices, liposomes and/or microspheres may also be used. These compositions may also optionally contain colourants and/or opacifying agents and may be of a composition such that they release the active ingredient(s) only, or preferentially, in a certain portion of the gastrointestinal tract, optionally, in a delayed manner.

The pharmaceutical compositions may comprise no more than about 70% w/w of pharmaceutically acceptable carrier and/or excipient and/or diluent, for example, no more than about 65% w/w of pharmaceutically acceptable carrier and/or excipients and/or diluent, or no more than about 60% w/w of pharmaceutically acceptable carrier and/or excipients and/or diluent, or no more than about 55% of pharmaceutically acceptable carrier and/or excipients and/or diluent, or no more than about 50% w/w of pharmaceutically acceptable carrier and/or excipients and/or diluent, or no more than about 45% w/w of pharmaceutically acceptable carrier and/or excipients and/or diluent, or no more than about 40% of w/w pharmaceutically acceptable carrier and/or excipients and/or diluent, or no more than about 35% w/w of pharmaceutically acceptable carrier and/or excipients and/or diluent. For example, the pharmaceutical composition may comprise at least about 1% w/w, or at least about 10% w/w, or at least about 15% w/w, or at least about 20% w/w, or at least about 25% w/w, or at least about 30% w/w of pharmaceutically acceptable carrier and/or excipients and/or diluent.

Liquid form preparations include solutions, suspensions, and emulsions, for example, water or water-propylene glycol solutions for oral administration. Liquid preparations can also be formulated in solution in aqueous polyethylene glycol solution. In certain embodiments, the active ingredient(s), i.e., garlic extracts, may be mixed with one or more pharmaceutically acceptable carriers and/or excipients and/or diluents, such as water and/or any of the following: solvent such as propylene glycol, alcohol; humectant such as glycerol; sweeteners such as liquid glucose, corn syrup and sucrose; artificial sweeteners such as aspartame, stevia and sucralose; preservatives such as benzoates and parabens; viscosity modifiers/thickeners such as gums and alginates; buffering agents; flavouring agents and colouring agents.

Also included are solid form preparations, for example, tablets, capsules, granules and powder, which are intended to be converted, shortly before use, to liquid form preparations for oral administration. Such liquid forms include solutions, suspensions, and emulsions. These particular solid form preparations are most conveniently provided in unit dose form and as such are used to provide a single liquid dosage unit. Alternatively, sufficient solid may be provided so that multiple individual liquid doses may be reconstituted when required, by measuring predetermined volumes of the solid form preparation as with a spoon, or other measuring device. The solid form preparations intended to be converted to liquid form may contain, in addition to the active material, flavourings, colourants, stabilizers, buffers, artificial and natural sweeteners, dispersants, thickeners, solubilising agents, and the like. The liquid utilized for preparing the liquid form preparation may be water, isotonic water, juices, milk, ethanol, and the like as well as mixtures thereof.

The terms "food", "foodstuff", "food supplement", "dietary supplement", "health supplement", "meal replacement product", "beverage" and "beverage supplement" used herein have the normal meanings for those terms, and are not restricted to pharmaceutical preparations. Other composition forms are also included within the present invention. These may, for example, include, a foodstuff precursor such as a rehydratable powder or a beverage precursor such as a powder dispersible in water, milk or other liquid.

Also included are solid form preparations which are intended to be combined with a food or foodstuff before oral consumption. The solid form preparations may be mixed into the food or foodstuff or applied to the food or foodstuff, e.g., by sprinkling onto the food or foodstuff. Such solid forms include powders, granules, pellets and the like. Such food of foodstuffs include, without limitation, prepared meals (cooked or fresh), soup, dairy based products (e.g., yoghurt, cream, crème-fraîche), flour based products such as bread and pasta, snack or convenience items such as snack bars (e.g., chocolate bars), confectionary products, and the like.

In certain embodiments, the food or foodstuff, and the like, comprises from about 0.1 wt. % to about 50 wt. % of the composition of the invention described herein, based on the total weight of the food or foodstuff, for example, from about 0.1 wt. % to about 40 wt. %, or from about 0.1 wt. % to about 30 wt. %, or from about 0.1 wt. % to about 20 wt. %, or from about 0.1 wt. % to about 15 wt. %, or from about 0.1 wt. % to about 10 wt. %, or from about 0.1 wt. % to about 8 wt. %, or from about 0.1 wt. % to about 6 wt. %, or from about 0.1 wt. % to about 4 wt. %, or from about 0.1 wt. % to about 2 wt. % of the composition of the invention described herein. In certain embodiments, the food or foodstuff, and the like, comprise at least about 0.2 wt. % of the compositions of the invention described herein, based on the total weight of the food or foodstuff, for example, at least about 0.5 wt. %, or at least about 1 wt. %, or at least about 5 wt. % of the composition of the invention described herein.

In certain embodiments, the composition is orally administered daily to the subject. Without wishing to be bound by theory, it is believed that the composition acts as an antimicrobial.

The amount of composition administered may be varied depending upon the requirements of the subject. For both therapeutic and non-therapeutic applications, the amount of composition administered may be varied depending upon the desired results, the requirements of the subject and the severity of the condition being treated. Determination of the proper amount/dosage for a particular situation is within the skill of the art. For example, for therapeutic applications a physician or veterinarian having ordinary skill in the art can readily determine and prescribe the effective amount of the pharmaceutical composition required. The total daily amount/dosage may be divided and administered in portions during the day if desired.

In general, a suitable daily dose of active agents in the composition according to the invention will be that amount which is the lowest dose effective to produce the desired effect, for example, a therapeutic effect, and/or to kill and/or inhibit or reduce the growth of microbes. It is contemplated that a wide range of doses may be used, due to the non-toxic nature of the composition. A person of ordinary skill in the art will understand that a suitable dose or dosage will typically vary from subject to subject, and will be dependent on factors such as the type of microbial infection and/or the severity of health conditions of the subject at the outset of administration of the composition. For example, the dose of active agents (i.e. garlic extracts) in the composition may be up to 15 g per day, for example, up to about 10 g per day, or up to about 5 g per day. In certain embodiments, the doses of active agents in the composition is in the range of 100 mg to about 3 g per day, which may be administered as two or three or more sub-doses administered separately at appropriate intervals throughout the day, optionally in unit dosage forms. In certain embodiments, the dose of active agents in the composition may be from about 200 mg to about 3 g of each garlic extract component per day, for example, from about 500 mg to about 3 g of each component per day, or from about 750 mg to about 2.5 g of each component per day, or from about 1000 mg to about 2000 mg of each component per day. In certain embodiments, the composition may be administered two or three times a day, optionally before, with, or after a meal. In certain embodiments, each dose of active agents is no more than about 5 g, for example, no more than about 3 g, for example, no more than about 2.5 g. Each dose of the garlic extracts in the composition may be combined with other conventional antimicrobial agents.

The compositions and pharmaceutical compositions described herein may be used in various therapeutic and non-therapeutic applications. For example, the compositions and pharmaceutical compositions described herein may be used in various cosmetic applications. For example, the compositions and pharmaceutical compositions described herein may be used in an in vitro or in an in vivo method. The methods may comprise administering the composition or pharmaceutical composition described herein to a subject. For example, the compositions and pharmaceutical compositions described herein may be used to provide one or more beneficial effects to a patient. For example, the compositions and pharmaceutical compositions described herein may be used as an antimicrobial. A used herein, the term "antimicrobial" means that the compositions and pharmaceutical compositions described herein may be used to kill microbes and/or to inhibit the growth of microbes and/or to reduce the growth of microbes.

In certain embodiments, the microbes may be selected from bacterial strain and fungal strain. The bacterial strains may, for example, be selected from gram-positive bacteria and gram-negative bacteria. The gram-positive bacteria may, for example, be selected from one or more of, *Clostridium perfringens, Listeria monocytogenes, Bacillus cereus, Enterococcus faecalis, Staphylococcus aureus*, Methicillin-resistant *Staphylococcus aureus, Streptococcus pneumoniae*, and *Streptococcus pyogenes*. The gram-negative bacteria may, for example, be selected from one or more of *Salmonella* Typhimurium, *Vibrio parahaemolyticus, Escherichia coli, Klebsiella pneumoniae, Pseudomonas aeruginosa, Acinetobacter baumannii* and *Campylobacteri jejuni*. The fungal strains may, for example, be selected from one or more of *Candida albicans, Candida glabrata, Aspergillus fumigatus*.

In certain embodiments, the subject is a human. In other embodiments, the subject is a mammal other than a human, such as non-human primates (e.g. apes, monkeys and lemurs), companion animals such as cats or dogs, working and sporting animals such as dogs, horses and ponies, farm animals such as pigs, sheep, goats, deer, oxen and cattle, and laboratory animals such as rodents (e.g. rabbits, rats, mice, hamsters, gerbils or guinea pigs).

In certain embodiments, the garlic extract components have a synergistic antimicrobial effect. The synergistic combinations of two garlic extracts can deliver an antimicrobial effect greater than the sum of the individual garlic extract antimicrobial and thus can provide an improved performance.

The synergistic effect of the composition or pharmaceutical composition can be determined by its Fractional Inhibitory Concentration Index (FICI), whereby FICI<1 indicates synergy, FICI=1 indicates additivity, FICI>1 indicates antagonism.

For example, the fractional inhibitory concentration index (FICI) value of the compositions and pharmaceutical compositions described herein may be less than 1.0, indicating that the combination of two garlic extracts has a synergistic effect. For example, the FICI of the compositions or pharmaceutical compositions described herein may be equal to or less than about 0.95, for example equal to or less than about 0.90, for example equal to or less than about 0.85, for example equal to or less than about 0.80, for example equal to or less than about 0.75, for example equal to or less than about 0.70, for example equal to or less than about 0.65, for example equal to or less than about 0.60.

The FICI of the compositions or pharmaceutical compositions described herein may, for example, be at least about 0.001, for example at least about 0.0018, for example at least about 0.002, for example at least about 0.005, for example at least about 0.01, for example at least about 0.02, for example at least about 0.05, for example at least about 0.1, for example at least about 0.2, for example at least about 0.5.

The FICI of the compositions or pharmaceutical compositions described herein can be calculated using the following formula:

FICI=(MIC of garlic extract 1 in combination/MIC of garlic extract 1 alone)+(MIC of garlic extract 2 in combination/MIC of garlic extract 2 alone)

The mean FICI can be calculated where more than one FICI is measured for one composition.

In certain embodiments, the compositions and pharmaceutical compositions disclosed herein are used in therapeutic applications. For example, the compositions and pharmaceutical compositions described herein may be administered to a subject to treat and/or prevent a microbial infection in a subject. For example, the compositions and pharmaceutical compositions described herein may be used to facilitate healing of damaged wound on the skin. For example, the compositions and pharmaceutical compositions described herein may be used to prevent microbial infection of damaged skin. For example, the compositions and pharmaceutical compositions described herein may be used to treat or prevent a microbial infection in the digestive system. For example, the compositions and pharmaceutical compositions described herein may be used to treat or prevent a microbial infection in the nasal or aural cavity of a subject. For example, the compositions and pharmaceutical compositions described herein may be used treat or prevent a microbial infection in the respiratory tract of a subject. For example, the compositions and pharmaceutical compositions described herein may be used as a urinary tract rinse, for example for urinary tract implant and kidney dialysis patients.

Thus, there is provided herein a therapeutic use of a composition or pharmaceutical composition described herein as an antimicrobial. There is also provided herein a composition or pharmaceutical composition as described herein for use as an antimicrobial. There is further provided herein a use of a composition or pharmaceutical composition as described herein in the manufacture of an antimicrobial medicament. There is further provided herein a therapeutic method for treating and/or preventing a microbial infection in a subject.

In certain embodiments, the compositions and pharmaceutical compositions disclosed herein are used in non-therapeutic applications.

For example, the compositions described herein may be used as an antimicrobial agent on non-living surfaces (e.g. as a disinfectant).

For example, the compositions and pharmaceutical compositions disclosed herein may be used for cosmetic applications, for example as an antimicrobial agent on living surfaces (e.g. skin). For example, the compositions and pharmaceutical compositions disclosed herein may be used as an antimicrobial in cosmetic skincare compositions or makeup compositions.

For example, the compositions described herein may be used as food and/or water additives for preservation and/or prevention of disease transmission. For example, the compositions described herein may be used in plant, fresh fruit and vegetable washes. The compositions described herein may reduce surface bacteria, extend shelf life and/or protect the surface from pest invasion in live crops or agricultural produce.

For example, the compositions described herein may be used as an antimicrobial on living surface. For example, the compositions described herein may be applied to the skin to kill microbes or inhibit growth of microbes for hygiene reasons (e.g. to prevent spread of disease). For example, the compositions described herein may be applied to the hands as a hand sanitizer. For example, the compositions described herein may be used as an oral rinse, for example to treat or prevent halitosis.

For example, the compositions described herein may be used for agricultural applications. For example, the compositions described herein may be used to treat or prevent infection of plant micro-wounds or may be used to reduce surface pathogens on a plant. For example, the compositions described herein may be used as bio-security sanitizer, for example for animal farm facilities. For example, the compositions described herein may be used for animal feed sterilization.

The expression "treating or preventing" and analogous terms used herein refers to all applications intended to remove or avoid the disorder or to relieve its symptoms, including preventive and curative care, as judged according to any of the tests available according to the prevailing medical practice. An intervention that aims with reasonable expectation to achieve a particular result but does not always do so is included within the expression "treating or preventing". An intervention that succeeds in slowing or halting progression of a disorder is included within the expression "treating or preventing".

The properties of the compositions and pharmaceutical compositions disclosed herein (e.g. the antimicrobial activity) may be determined in vivo or in vitro. An in vitro method for determining the antimicrobial activity is described in the Examples section below.

The compositions and pharmaceutical compositions described herein may be prepared by combining a first garlic extract and a second garlic extract and optionally any one or more of the other ingredients described herein, such as one or more further garlic extracts, dietary fibre, nutrients, biologically active agents and pharmaceutical excipients and/or carriers and/or diluents. The components are combined in suitable amounts to obtain a composition having the desired quantity of each component. Each component may be combined with one or more other components in any order and combination suitable to obtain the desired product. For example, each component may be combined by mixing (e.g. the first and second garlic extracts may be combined by mixing). Such methods are well known in the art, for example, methods known in the food industry (e.g. those used in the preparation of health food bars and the like) and methods known in the pharmaceutical industry. The composition may be prepared in the dry solid form, for example, powder form, and subject to further processing step depending on the types of the formulation for the intended finished products. The methods may further comprise a forming step, wherein the mixture is moulded, pressed, spray dried or otherwise formed into a shape (e.g. bar, ball, pellet, clusters, tablet), preferably with dimensions and/or textures suitable for consumption by a human or other mammalian animal of the types described herein.

The invention will now be described in detail by way of reference only to the following non-limiting examples.

EXAMPLES

Example 1: Checkerboard Dilution Assay for Evaluation of Combined Antimicrobial Effects of Garlic Extracts 1. The checkerboard dilution assay was determined using minimum inhibitory concentration (MIC) of individual garlic extracts to evaluate the combined antimicrobial effects of the garlic extracts. The MIC test and checkerboard dilution assay were performed using 96 well (12×8 well) microtiter plate.
2. In the MIC test, a two-fold dilution series of garlic extracts were prepared with dilutions being made in growth media. Different types of growth media were used for different strains. Cation-adjust Meuller Hinton Broth (CAMHB) was used for both gram-positive and gram-negative strains except for *Streptococcus* strains, *C. perfringens*, *C. jejuni* and *L. monocytogenes*. CAMHB+2.5% Lysed Horse Blood (LHB) used for *Streptococcus* strains, *L. monocytogenes* and *C. jejuni* while Schaedler anaerobe broth used for *C. perfringens*. For fungal strains, Roswell Park Memorial Institute—1640 (RPM1-1640) with 2% w/v D-Glc and 0.165 mol/L MOPS (RPMI-MOPS) broth was used.
3. The two-fold dilutions for the MIC test were made in a 96 well microtiter plate such that each well has a final volume of 100 µl garlic extract and media. The first well has, for example, a concentration of 150 mg/ml of garlic extract. Then, 100 µl of the cell suspension (adjusted to contain 2 to $5.0 \times 10^5$ cells/ml) was added into each well.
4. The plate containing aerobic bacteria strains was incubated at 37° C. for 24 hours while the plate containing fungal strain was incubated at 35° C. for 48 hours. For *C. perfringens*, the plate was incubated at 37° C. for 24 hours under anaerobic condition whereas *C. jejuni* was incubated at 37° C. for 48 hours under microaerobic condition (10% $CO_2$). After incubation, the MIC was taken to be the lowest active concentration that inhibited growth of the test strain, which was observed as no visible microbial growth.
5. To construct a checkerboard dilution assay, the first garlic extract for example DGPE was diluted using two-fold dilutions and 50 µl of the extract was added to each well at longitudinal direction. Then the second garlic extract for example BGPE was diluted using two-fold dilutions and 50 µl of the extract was added to each well at latitudinal direction. The first well has, for example, a concentration of 37.5 mg/ml of DGPE and 37.5 mg/ml of BGPE (for *E. coli*, MRSA, *P. aeruginosa*, *K. pneumoniae*, *S. pyogenes*, *S. pneumoniae* & *A. baumannii*). For example, the first well has 18.75 mg/ml of DGPE and 9.375 mg/ml of BGPE (for *B. cereus*, *C. perfringens*, *C. Jejuni*, *V. parahaemolyticus*, *L. monocytogenes* and *A. fumigatus*). For example, the first well has 18.75 mg/ml of DGPE and 9.375 mg/ml of BGPE (for *E. faecalis*, *S. Typhimurium*, *C. albicans* & *C. glabrata*). After that, 100 µl of the cell suspension was added to the well.
6. The plate containing bacteria strains except for *C. perfringens* & *C. jejuni* was incubated at 37° C. for 24 hours under aerobic conditions while plate containing fungal strain was incubated at 35° C. for 48 hours under aerobic condition. For *C. perfringens*, the plate was incubated at 37° C. for 24 hours under anaerobic condition whereas *C. jejuni* was incubated at 37° C. for 48 hours under microaerobic condition.
7. After the incubation duration, the MIC of combined extract effect was visually assessed where wells without any visual turbidity was considered no growth. The MIC was taken to be the lowest active concentration that inhibited growth of the test strain, which was observed as no visible microbial growth compared to control culture.
8. The interaction of 2 different garlic extracts was evaluated using the fractional inhibitory concentration index (FICI). The FICI value was calculated for each agent by dividing the inhibitory concentration of each drug when used in combination with its corresponding MIC value. The following formula was used to calculate FICI:

$$FICI = \frac{MIC \text{ of garlic extract 1 in combination}}{MIC \text{ of garlic extract 1 alone}} + \frac{MIC \text{ of garlic extract 2 in combination}}{MIC \text{ of garlic extract 2 alone}}$$

9. Mean FICI was calculated for compositions where more than one FICI was measured.

Based on the interpretation standard published by Kull et al., 1961, the following calculations were formulated and used to describe the interpretations.

| | FICI | Description |
|---|---|---|
| Synergism | <1 | At least 4X MIC reduction of on 1 fraction and 2-4X reduction in the other fraction when apply together. |
| Additive | 1 | At least 2X MIC reduction of every fraction when applied together. |
| Antagonistic | >1 | Combination causes at least 2X fold MIC reduction of only 1 fraction, with potency of another fraction remains unaffected. No changes of potency of every fraction when apply together. |

The results of the combined antimicrobial effects of two garlic extracts are shown in Table 1 below.

TABLE 1

| Strains tested | Mean FIC | interpretation |
|---|---|---|
| E. coli | 0.2756 | Synergistic |
| K. pneumoniae | 0.4995 | Synergistic |
| P. aeruginosa | 0.5877 | Synergistic |
| A. baumannii | 0.4297 | Synergistic |
| MRSA | 0.8218 | Synergistic |
| S. pneumoniae | 0.0371 | Synergistic |
| S. pyogenes | 0.1681 | Synergistic |

TABLE 1-continued

| Strains tested | Mean FIC | interpretation |
| --- | --- | --- |
| C. perfringens | 0.3534 | Synergistic |
| S. Typhimurium | 0.2499 | Synergistic |
| V. parahaemolyticus | 0.0018 | Synergistic |
| L. monocytogenes | 0.0210 | Synergistic |
| E. faecalis | 0.8936 | Synergistic |
| C. jejuni | 0.0988 | Synergistic |
| B. cereus | 0.1463 | Synergistic |
| C. albicans | 0.9365 | Synergistic |
| C. glabrata | 0.9355 | Synergistic |
| A. fumigatus | 0.6207 | Synergistic |

It was surprisingly found that the two garlic extracts used, work synergistically to provide an antimicrobial effect.

The invention claimed is:

1. A therapeutic or non-therapeutic method for inhibiting the growth of and/or reducing the number of one or more microbes, the method comprising:
contacting the microbes with a composition comprising a first garlic extract and a second garlic extract different from the first garlic extract, wherein the first garlic extract is an aged garlic extract, and the second garlic extract is a non-aged garlic extract, wherein the first garlic extract comprises equal to or greater than 0.5% (w/w) polyphenol and the second garlic extract comprises equal to or greater than 0.5% (w/w) allicin.

2. A method according to claim 1, wherein the microbe is selected from one or more of Candida albicans, Candida glabrata, Aspergillus fumigatus, Clostridium perfringens, Salmonella Typhimurium, Listeria monocytogenes, Vibrio parahaemolyticus, Escherichia coli, Klebsiella pneumoniae, Pseudomonas aeruginosa, Acinetobacter baumannii, Bacillus cereus, Enterococcus faecalis, Campylobacter jejuni, Staphylococcus aureus, Methicillin-resistant Staphylococcus aureus, Streptococcus pneumoniae and Streptococcus pyogenes.

3. The method according to claim 1, wherein the composition comprises an animal feed or a feed additive.

4. The method according to claim 1, wherein the aged garlic extract is a black garlic extract, caramelised garlic extract, and/or fermented garlic extract.

5. The method according to claim 1, wherein the non-aged garlic extract comprises deodourised garlic extract and/or deodourised garlic powder extract.

6. The method according to claim 1, wherein the non-aged garlic extract comprises at least 3 wt % allicin.

7. The method according to claim 1, wherein the aged garlic extract comprises at least 5 wt % polyphenol.

8. The method according to claim 1, wherein the weight ratio of the first garlic extract to the second garlic extract ranges from 1:2000 to 100:1.

9. The method according to claim 1, wherein the first garlic extract is a black garlic extract and the second garlic extract is a deodourised garlic extract, and the weight ratio of the first to the second garlic extract is 16:1 to 1:16.

10. The method according to claim 1, wherein the composition comprises alliin, γ-glutamylcysteine, S-allyl-L-cysteine, or any combination of two or more thereof.

11. The method according to claim 1, wherein the composition comprises:
equal to or greater than 1.5% (w/w) total thiosulfinates; and/or
equal to or greater than 3.2% (w/w) alliin; and/or
equal to or greater than 3.0% (w/w) γ-glutamylcysteine; and/or
equal to or greater than 0.6% (w/w) total sulfur; and/or
equal to or greater than 0.15% (w/w) S-allyl-L-cysteine.

12. The method according to claim 1, wherein the composition is a foodstuff, a food supplement, a beverage, a beverage supplement, a dietary supplement, a health supplement, a meal replacement product, a food additive, an animal feed, or a feed additive.

13. The method according to claim 1, wherein the composition is administered to a subject for treating or preventing a microbial infection in the subject.

14. The therapeutic method according to claim 13, wherein the microbe is selected from one or more of bacteria and fungi.

15. A method according to claim 14, wherein the microbe is selected from one or more of Candida albicans, Candida glabrata, Aspergillus fumigatus, Clostridium perfringens, Salmonella typhimurium, Listeria monocytogenes, Vibrio parahaemolyticus, Escherichia coli, Klebsiella pneumoniae, Pseudomonas aeruginosa, Acinetobacter baumannii, Bacillus cereus, Enterococcus faecalis, Campylobacter jejuni, Staphylococcus aureus, Methicillin-resistant Staphylococcus aureus, Streptococcus pneumoniae and Streptococcus pyogenes.

16. The method according to claim 13, wherein the composition comprises an animal feed or a feed additive.

17. The method according to claim 1, wherein the aged garlic extract is formed from garlic stored in water or alcohol before extraction.

18. The method according to claim 1, wherein each of the first garlic extract and the second garlic extract is an aqueous or non-aqueous solvent extract.

19. The method according to claim 9, wherein the first garlic extract in combination with the second garlic extract provides a synergistic antimicrobial effect.

20. The method according to claim 19, wherein the synergistic antimicrobial effect is greater than a sum of an individual garlic extract antimicrobial effect of the first garlic extract and the second garlic extract.

* * * * *